United States Patent [19]

Tal

[11] Patent Number: 5,516,979
[45] Date of Patent: May 14, 1996

[54] COTTON HYBRID

[75] Inventor: Yehiel Tal, Kiryat Gat, Israel

[73] Assignee: Hazera (1939) Ltd., Mivhor, Israel

[21] Appl. No.: 238,868

[22] Filed: May 6, 1994

[30] Foreign Application Priority Data

May 6, 1993 [IL] Israel ........................................ 105619

[51] Int. Cl.$^6$ ................................ A01H 5/00; A01H 1/02
[52] U.S. Cl. .................................. 800/200; 800/DIG. 27; 800/DIG. 63; 47/58; 47/DIG. 1
[58] Field of Search ............................ 800/200, DIG. 27, 800/DIG. 63; 47/58, 58.03, DIG. 1

[56] References Cited

PUBLICATIONS

Triplett, B. 1990, Textile Research Journal, Mar. 1990, pp. 143–148.
Singh et al. 1990, Indian J. Genet. 50(4): 396–399.
Endrizzi et al. 1991, J. Hered. 82(1):53–57.
Ayub et al. 1991, Sarhad J. Agric. 7(6):707–716.

*Primary Examiner*—David T. Fox
*Attorney, Agent, or Firm*—Dennison, Meserole, Pollack & Scheiner

[57] ABSTRACT

An heterozygous tetraploid first generation (F1) cotton hybrid wherein only one parent bears the dominant alleles of the gene $N_1$, and that parent is homozygous for $N_1$, and the other parent has greater than 25% lint percent.

3 Claims, No Drawings

COTTON HYBRID

FIELD OF THE INVENTION

The present invention relates to cotton seeds having abundant lint which are naked or fuzzless seeds after ginning.

BACKGROUND OF THE INVENTION

Cotton plants having a variety of different seed characteristics are known. Of particular interest are cotton plants having so-called naked seeds, seeds from which all the lint can be easily removed during ginning without breaking the fibers or creating seed coat fragments.

Naked seeds have a number of advantages over fuzzy seeds (which retain a fuzz of very short fibers even after ginning). First, naked seeds can be ginned by Roller Gins which cause less damage or tearing to the lint during ginning, thereby retaining the original length of the lint fibers. Second, the less fuzz on the seed, the more efficient the ginning process. This is due to the fact that the fuzz creates resistance to the roller gin during ginning. Therefore, varieties having fuzzy seeds are generally ginned by Saw Gins, which tend to hear the fibers, thus reducing the length and quality of the lint.

The third factor is the ease of removal of lint fibers from the seed. Naked seeds generally require lower force to remove the fibers than fuzzy seeds. Greater resistance to ginning can lead not only to torn fibers, but also to a broken seed coat, especially when the seeds have a relatively weak coat. This causes contamination of the lint with seed coat fragments during removal of the lint. This seed coat fragmentation is minimal in naked seeds.

Several genes are known to control the presence or absence and quantity of fuzz, whose effects are influenced by other genes, so-called modifiers, on the genome. Two of them will be discussed herein. The first is the recessive gene $n_2n_2$. This gene is characteristic of most of the commercial cotton varieties of the species G. barbadense. Here, due to the recessive nature of the gene, the naked seed characteristics result only in a variety homozygous for the recessive allele of this gene. In these strains, generally there is substantial lint, i.e., above 30%, and the seed cotton can be ginned by a roller gin. The seeds are never totally naked, but retain fuzz at least at the tip. In some cases, the amount of fuzz remaining on the seed, especially on the chalazal end, causes some tearing of the seed coat during ginning. Furthermore, the seeds are not homogeneous, in that those which are formed higher up on the plant are more naked than those which were formed on lower branches. These strains are also problematic with regard to planting, since all the fuzz must be removed from the seed in order to plant it using conventional planting machines.

The other gene is the dominant gene $N_1$. This gene is much less common, but its results are more powerful. When the strain is homozygous $N_1$, the most advantageous results in terms of a naked seed are produced. The presence of four dominant alleles of $N_1$ results in a totally naked seed, even at the tip, sometimes called a fuzzless seed. And the seeds are homogeneous, in that all the seeds on the plant have the same characteristics. However, this has a corresponding disadvantage in that the quantity of lint is extremely limited, i.e., generally between 0 and 15%, so that such a strain is not commercially viable.

Today, known varieties of cotton (except hybrids) are all homozygous, in order to provide uniformity of the variety. Thus, utilization of the gene $N_1$ is basically impossible due to the low quantity of lint, regardless of the total genetic background, in most cases. The search for such a strain or variety with high lint percent would be a long and difficult process and not likely to be successful.

Furthermore, in developed countries, so far the obstacles to seed production of cotton hybrids have ruled out the possibility of developing commercial hybrids and utilizing genes in the heterozygous state for commercial purposes. This has only been done in India, where all the crossing is done by hand.

SUMMARY OF THE INVENTION

It is an object of the present invention to provide a tetraploid cotton hybrid which grows into a plant producing seeds having a substantial quantity of lint which is easily removable, and which becomes a totally fuzzless seed after ginning.

There is thus provided in accordance with the present invention an heterozygous tetraploid first generation (F1) cotton hybrid wherein only one parent bears the dominant alleles of the gene $N_1$, and that parent is homozygous for $N_1$, and the other parent has greater than 25% lint percent.

There is further provided according to the invention plants of such an hybrid.

According to one embodiment, one of the parents is of the species G. barbadense.

There is further provided a method of producing a tetraploid, heterozygous first generation cotton hybrid consisting of crossing a cotton genotype homozygous for the dominant allele of gene $N_1$ with a cotton genotype which does not include any dominant $N_1$ alleles but which produces seeds having more than 25 lint percent. Preferably the method includes crossing the cotton genotype homozygous for $N_1$ with a genotype of the species G. barbadense or G. hirsutum. The resulting F1 plant population is homogeneous for the characteristics of fuzzless seed and lint percent.

DETAILED DESCRIPTION OF THE INVENTION

The present invention relates to a tetraploid hybrid cotton plant which produces seeds having a commercial quantity of lint, i.e., above 25%, and which are fuzzless naked seeds. Such a cotton plant can be produced by crossing two cotton genotypes, one and only one of which has the dominant alleles of the $N_1$ gene, and the other which has no dominant alleles of the $N_1$ gene but its plant produces seeds having high lint percent. One example is a plant grown from seeds produced by sexual crossing of two such cotton genotypes. It will be appreciated that the quantity of lint and the quality of the lint depend upon the specific parents selected for crossing.

The parent which has the dominant allele of the $N_1$ gene must be homozygous (i.e., all four alleles are $N_1$.) The second parent must not have dominant $N_1$ alleles at all but rather must have a relatively high percentage of lint, i.e., above about 25%. According to one embodiment, the species selected for one of the parents is G. barbadense, which is usually homozygous for the recessive allele of gene $n_2n_2$. According to another preferred embodiment, the parent which has the dominant alleles of $N_1$ can be either of the species G. hirsutum or G. barbadense.

It is a particular feature of the present invention that the resulting first generation (F1) hybrid plants are heterozygous and have the preferred characteristics of both parents, i.e., lint percent above 25% and a totally fuzzless seed. When at least one parent is of the species barbadense, the resulting plants have high lint quality as well as high lint percent.

It will be appreciated by those skilled in the art that the second generation (F2) are not homogeneous and do not retain the characteristics of the first generation mentioned above. Rather, self-pollination results in an F2 population heterogeneous for these characteristics.

Those skilled in the art will appreciate that any means of crossing the above-described genotypes is operative according to the invention. By way of example only, two examples of sexual crosses according to the invention are set forth below.

Example I

Interspecific Cross

One plant (genotype), which acts as the female parent, is called #172 and belongs to the tetraploid species *G. hirsutum*. It is homozygous for the gene $N_1$ for the dominant allele (4 alleles). The lint percentage of #172 ranges between 5 and 7%, according to the location of the boll on the plant. This plant does not have the recessive alleles $n_2n_2$.

A second plant (genotype), which acts as the male parent, is called #2209 and belongs to the species *G. barbadense*. It has a lint percentage in the range of 35 to 38%, according to the boll location on the plant. This plant has naked (but not fuzzless) seeds because it is homozygous for the recessive allele $n_2$ and has long and strong fibers of high quality.

The resulting hybrid first generation from this cross is a homogeneous plant population called F1-1722. All the plants have fuzzless seeds as a result of the presence of two dominant $N_1$ alleles on their genome. At the same time, they have a lint percent between 30 and 37% depending on the size and location of the boll on the plant.

The result of this interspecific cross is an F1 population having a uniformly high quality of lint which is due to the contribution of the male parent of the species barbadense.

Example II

Intraspecific Cross

The female parent (genotype) is the same #172 described above in Example I.

The male parent (genotype) is also of the species *G. hirsutum*, known as #D6. The seeds of #D6 are covered with fuzz and do not have the recessive allele n2 or the dominant allele N1. The lint percent ranges from 37 to 40%, depending on the size and location of the boll on the plant.

The resulting hybrid first generation (F1) plant of this cross is called F1-172D6 and is characterized by the uniformity of the naked seed of the plants caused by the presence of the dominant allele N1 in the heterozygous state (2 alleles). The lint percent is similar to the parent D6. In addition, the quality of the fibers of the F1 plants is similar to most of the plants of the species *G. hirsutum*. It is lower in quality of lint than the interspecific hybrids of Example I with regard to length, strength and fineness of the fibers. However, the characteristics of the smooth fuzzless seed permit ginning of the seed cotton of these plants by roller gins. This permits one to produce fibers of better quality for spinning without seed coat fragments and without damage to the length of the fibers.

As stated above, self-fertilization of the F1 hybrid plants of either Example I and II results in a completely non-uniform second generation which is not acceptable from a commercial point of view.

It will be appreciated by those skilled in the art that the invention is not limited to what has been described hereinabove by way of example. Rather, the scope of the invention is limited solely by the claims which follow.

I claim:

1. A first generation (F1) tetraploid cotton hybrid having above 25% lint percent wherein only one parent genotype bears the dominant alleles of the gene $N_1$, and that parent is homozygous for $N_1$, said hybrid being heterozygous for the gene $N_1$, wherein two alleles out of four are dominant, and wherein the parent genotype which does not bear the dominant allele $N_1$ produces seed cotton having a lint percent above 25%;

wherein said parent which produces seed cotton having a lint percent above 25% is of the species *G. barbadense* or *G. hirsutum*;

wherein said parent which bears the dominant allele $N_1$ is of the species *G. hirsutum* or *G. barbadense*; and wherein said hybrid results from the sexual crossing of said two parents.

2. A tetraploid hybrid cotton plant according to claim 1 and having a substantially fuzzless seed with more than 25% lint percent.

3. A method of producing a tetraploid, heterozygous first generation cotton hybrid according to claim 1 comprising:

crossing a parent cotton genotype homozygous for the dominant allele of the gene $N_1$ which is selected from the species *G. barbadense* or *G. hirsutum*, with a parent cotton genotype which does not have any dominant $N_1$ alleles and which produces seed cotton having a lint percent greater than 25% which is selected from the species *G. barbadense* or *G. hirsutum*.

* * * * *